US009427168B2

(12) United States Patent
Edwards et al.

(10) Patent No.: US 9,427,168 B2
(45) Date of Patent: Aug. 30, 2016

(54) METHODS, SYSTEMS, AND APPARATUS FOR IDENTIFICATION, CHARACTERIZATION, AND TREATMENT OF ROTORS ASSOCIATED WITH FIBRILLATION

(71) Applicant: AFTx, Inc., Westminster, CO (US)

(72) Inventors: Jerome Edwards, Erie, CO (US); Bao Nguyen, Westminster, CO (US); Paul Kessman, Lakewood, CO (US); Thomas Kurian, St. Louis, MO (US)

(73) Assignee: AFTx, Inc., Westminster, CO (US)

( * ) Notice: Subject to any disclaimer, the term of this patent is extended or adjusted under 35 U.S.C. 154(b) by 0 days.

(21) Appl. No.: 14/703,532

(22) Filed: May 4, 2015

(65) Prior Publication Data
US 2015/0313491 A1    Nov. 5, 2015

Related U.S. Application Data

(63) Continuation-in-part of application No. 14/466,588, filed on Aug. 22, 2014, now Pat. No. 9,078,583.

(60) Provisional application No. 61/988,650, filed on May 22, 2013, provisional application No. 61/988,651, filed on May 5, 2014.

(51) Int. Cl.
*A61B 5/04* (2006.01)
*A61B 5/00* (2006.01)
(Continued)

(52) U.S. Cl.
CPC ............ *A61B 5/044* (2013.01); *A61B 5/0044* (2013.01); *A61B 5/042* (2013.01); *A61B 5/04007* (2013.01); *A61B 5/04012* (2013.01);
(Continued)

(58) Field of Classification Search
USPC .......................................... 600/508–509, 515
See application file for complete search history.

(56) References Cited

U.S. PATENT DOCUMENTS 9,078,583 B2    7/2015    Edwards et al.
2006/0235476 A1    10/2006    Gunderson et al.
(Continued)

FOREIGN PATENT DOCUMENTS

WO    WO 2012/092016 A1    7/2012

OTHER PUBLICATIONS

Go, Alan S., et al. "Prevalence of Diagnosed Atrial Fibrillation in Adults: National Implications for Rhythm Management and Stroke Prevention: the AnTicoagulation and Risk Factors in Atrial Fibrillation (ATRIA) Study." JAMA 2001; 285:2370-2375.
(Continued)

*Primary Examiner* — Nicole F Lavert
(74) *Attorney, Agent, or Firm* — Cooley LLP

(57) ABSTRACT

Some embodiments described herein relate to a method that includes defining an electro-anatomical model of a heart. The electro-anatomical model can include conduction patterns for multiple patterns or phases identified by a measurement instrument. The electro-anatomical model can also include a voltage map of the heart. A portion of the heart containing a rotor can be identified based on circulation in one phase of the model. The rotor can be determined to be stable based on that portion of the heart having circulation in another phase of the model. The rotor can be characterized as a substrate rotor based on the rotor being stable and based on the voltage or a change in voltage at the portion of the heart containing the rotor. The rotor can be treated or ablated when the rotor is determined to be a substrate rotor.

24 Claims, 5 Drawing Sheets

(51) Int. Cl.
| | |
|---|---|
| A61B 5/044 | (2006.01) |
| A61B 5/042 | (2006.01) |
| A61B 18/14 | (2006.01) |
| A61B 5/053 | (2006.01) |
| A61B 18/00 | (2006.01) |

(52) U.S. Cl.
CPC ........... *A61B5/0422* (2013.01); *A61B 5/0536* (2013.01); *A61B 5/0538* (2013.01); *A61B 5/4836* (2013.01); *A61B 18/14* (2013.01); *A61B 18/1482* (2013.01); *A61B 18/1492* (2013.01); *A61B 2018/00351* (2013.01); *A61B 2018/00577* (2013.01)

(56) References Cited

U.S. PATENT DOCUMENTS

| | | | |
|---|---|---|---|
| 2007/0208260 | A1* | 9/2007 | Afonso .............. A61B 5/04012 600/508 |
| 2010/0168560 | A1 | 7/2010 | Hauck et al. |
| 2011/0144509 | A1 | 6/2011 | Kahlert et al. |
| 2011/0230775 | A1 | 9/2011 | Barley et al. |
| 2012/0209343 | A1 | 8/2012 | Efimov et al. |
| 2013/0096394 | A1* | 4/2013 | Gupta ................ A61B 5/04012 600/301 |

OTHER PUBLICATIONS

Miyasaka, Yoko, et al. "Secular Trends in Incidence of Atrial Fibrillation in Olmsted County, Minnesota, 1980 to 2000, and Implications on the Projections for Future Prevalence." Circulation Lippincott Williams & Wilkins, 2006; 114:119-125.

Haissaguerre, Michel, et al. "Spontaneous Initiation of Atrial Fibrillation by Ectopic Beats Originating in The Pulmonary Veins." N Engl J Med 1998; 339:659-666.

Wilber David J., et al, "Comparison of Antiarrhythmic Drug Therapy and Radiofrequency Catheter Ablation in Patients With Paroxysmal Atrial Fibrillation: A Randomized Controlled Trial." JAMA American Medical Association, 2010; 303:333-340.

Calkins, Hugh, et al. 2012 HRS/EHRA/ECAS Expert Consensus Statement on Catheter and Surgical Ablation of Atrial Fibrillation: Recommendations for Patient Selection, Procedural Techniques, Patient Management and Follow-up, Definitions, Endpoints, and Research Trial Design. Eurospace, 2012 14, 528-606.

Brooks, Anthony G, et al.: "Outcomes of Long-Standing Persistent Atrial Fibrillation Ablation: A Systematic Review." Heart Rhythm, 2010; 7:835-846.

Narayan, Sanjiv M., et al. "Computational Mapping Approach Identifies Stable and Long-Lived Electrical Rotors and Focal Sources in Human Atrial Fibrillation." PLos One, 2012.

Cuculich, Phillip S., et al. "Noninvasive Characterization of Epicardial Activation in Humans With Diverse Atrial Fibrillation Patterns." Circulation, Lippincott Williams & Wilkins, 2010; 122:1364-1372.

Jadidi, Amir S., et al. "Inverse Relationship Between Fractionated Electrograms and Atrial Fibrosis in Persistent Atrial Fibrillation: Combined Magnetic Resonance Imaging and High-Density Mapping." Journal of the American College of Cardiology 2013; 62:802-812.

Miller, John M., et al. "Initial Independent Outcomes From Focal Impulse and Rotor Modulation Ablation for Atrial Fibrillation: Multicenter Firm Registry." J. Cardiovasc. Electrophysiol. 2014; 25:921-929.

Narayan, Sanjiv M., et al. "Treatment of Atrial Fibrillation by The Ablation of Localized Sources: Confirm (Conventional Ablation for Atrial Fibrillation With or Without Focal Impulse and Rotor Modulation) Trial." Journal of the American College of Cardiology 2012; 60:628-636.

Haissaguerre, Michel, et al. "Driver Domains in Persistent Atrial Fibrillation." Circulation, Lippincott Williams & Wilkins, 2014; 130:530-538.

Kurian, Thomas et al., "Identification of drivers in patients with persistent atrial fibrillation using a novel spatiotemporal computational algorithm integrated with electroanatomic mapping," Abstract, The Boston AF Symposium, Apr. 9, 2014 pp. 564-565.

Karthikeyan, Umapathy et al., "Phase Mapping of Cardiac Fibrillation," Circ Arrhythm Electrophysiol, 2010; 3:105-114.

Kremen, V. et al., "Comparison of Several Classifiers to Evaluate Endocardial Electrograms Fractionation in Human," 31$^{st}$ Annual International Conference of the IEEE EMBS, Sep. 2009; 2502-2505.

Search Report and Written Opinion for International Patent Application No. PCT/US2015/029031, mailed Aug. 13, 2015.

Office Action for U.S. Appl. No. 14/466,588, mailed Nov. 17, 2014.

International Search Report and Written Opinion for International Application No. PCT/US2014/052356, mailed Jan. 20, 2015 (16 pages).

Pandit, Sandeep V., et al.; Rotors and the Dynamics of Cardiac Fibrillation, Circulation Research Journal of the American Heart Association, Mar. 1, 2013, pp. 849-862, 7272 Greenville Ave., Dallas, TX 75231.

* cited by examiner

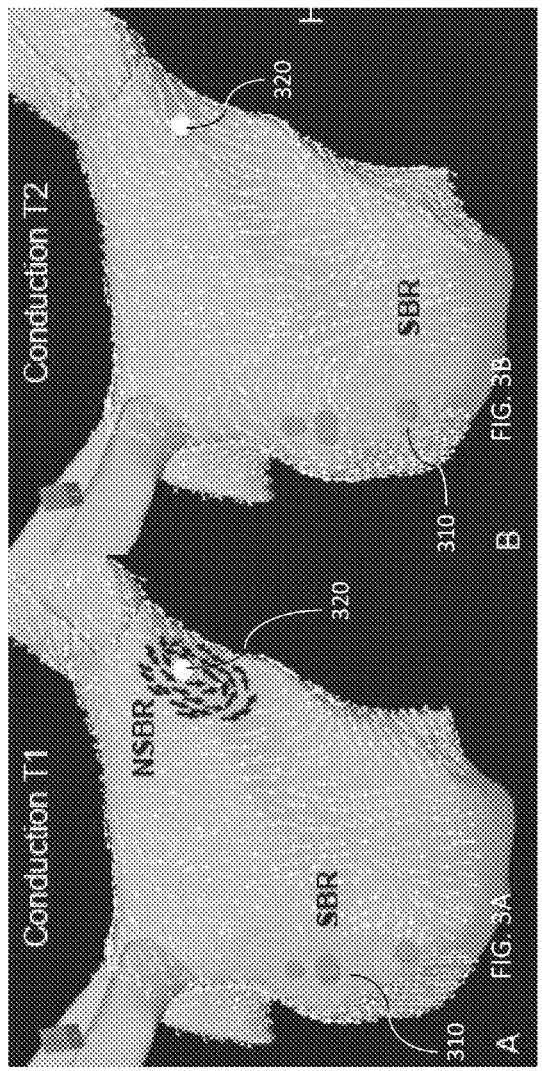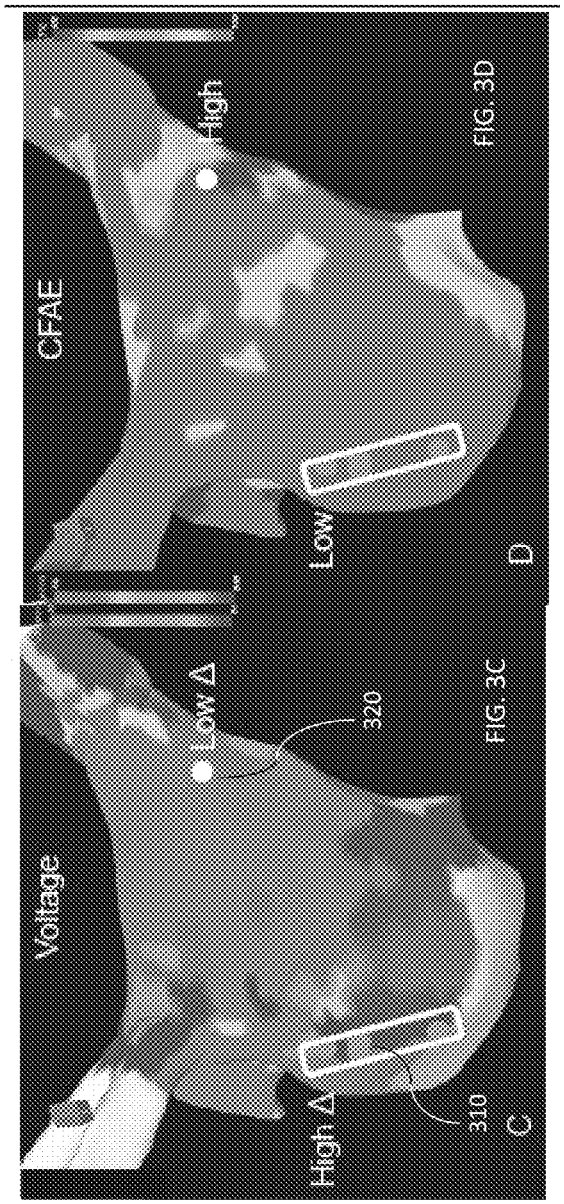

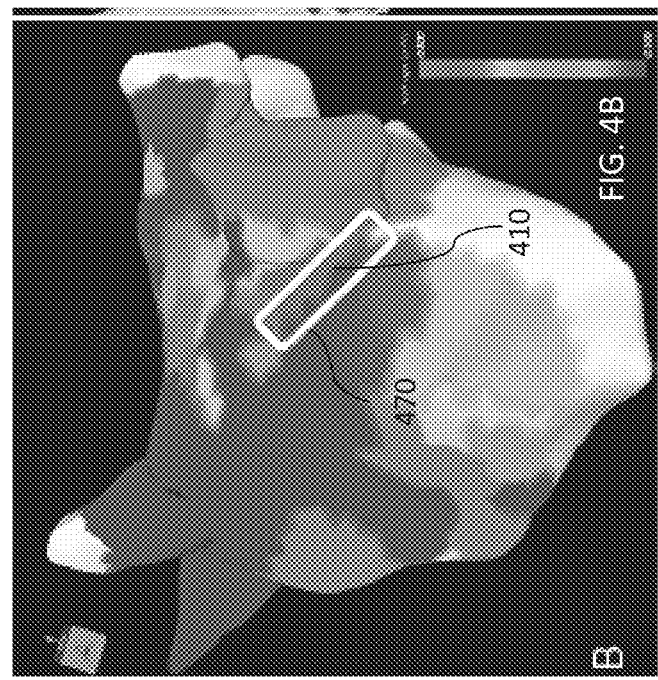
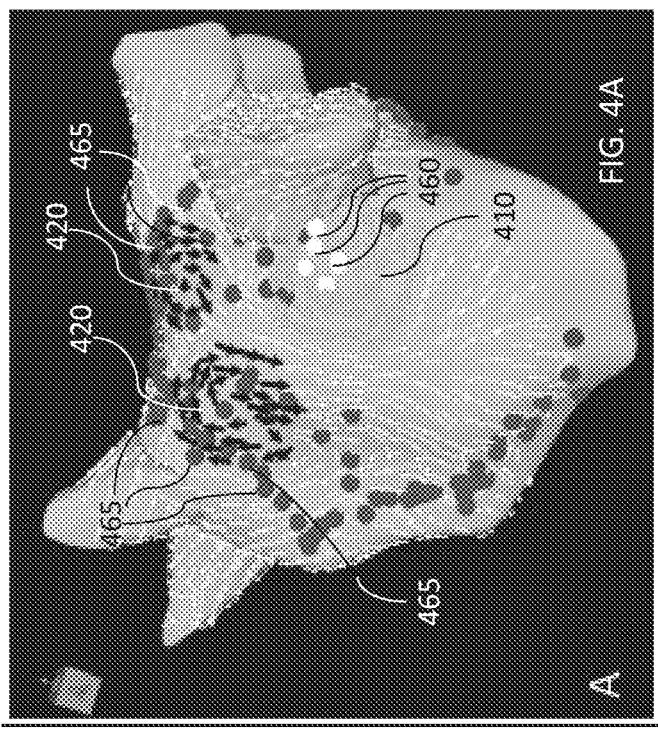

METHODS, SYSTEMS, AND APPARATUS FOR IDENTIFICATION, CHARACTERIZATION, AND TREATMENT OF ROTORS ASSOCIATED WITH FIBRILLATION

CROSS REFERENCE TO RELATED APPLICATIONS

This application claims the benefit of provisional U.S. Patent Application No. 61/988,651, filed May 5, 2014, under 35 U.S.C. §119(e), the disclosure of which is hereby incorporated by reference in its entirety.

BACKGROUND

This application relates generally to methods, systems, and apparatus for identifying, characterizing, and treating rotors associated with fibrillation. Some methods described herein are suitable for distinguishing between and/or classifying substrate rotors and non-substrate rotors. Substrate rotors may be associated with and/or may significantly influence arrhythmias, while non-substrate rotors may not be strongly associated with arrhythmias. Some embodiments described herein can include treating substrate rotors and/or not treating non-substrate rotors, which can improve cardiac outcomes.

In the last few years, scientific understanding of atrial fibrillation has discovered that the electrical activity in the heart during atrial fibrillation is not complete chaos as once accepted under the Moe model of random wavelets of electrical activity causing atrial fibrillation. There are indeed local organized electrical drivers of atrial fibrillation. Recent research has revealed that electrical patterns in the heart commonly referred to as rotors play an important role in many cases of fibrillation, particularly persistent atrial fibrillation. Currently, surgical systems are available that modify cardiac tissue during treatment using RF energy, cryo, laser, direct current, stem-cells, or drugs. In some situations modifying, ablating, or "burning" a rotor can significantly improve cardiac function.

Known surgical techniques, however, have inconsistent results; ablation of some rotors results in significant changes in heart rhythm, while ablation of other rotors does not have a significant effect. A need therefore exists for methods, systems, and apparatus for identifying and characterizing rotors.

SUMMARY

Some embodiments described herein relate to a method that includes defining an electro-anatomical model of a heart. The electro-anatomical model can include conduction patterns for multiple patterns or phases identified by a measurement instrument. The electro-anatomical model can also include a voltage map of the heart. A portion of the heart containing a rotor can be identified based on circulation in one phase of the model. The rotor can be determined to be stable based certain characteristics including stability of the rotor over time and/or across phases, the rotor presenting along borders of voltage transition, and/or negative association with complex fractionated electrograms in the region of the rotor's presentation. The rotor can be treated or ablated when the rotor is determined to be a substrate rotor.

BRIEF DESCRIPTION OF THE DRAWINGS

FIGS. 3A and 3B are two phases of an example of an electro-anatomical model of a left atrium showing cardiac conduction patterns, according to an embodiment.

FIG. 3C is an example of an electro-anatomical model of the left atrium of FIGS. 3A and 3B showing a voltage map.

FIG. 3D is an example of an electro-anatomical model of the left atrium of FIGS. 3A-3C showing a complex fractionation map.

FIG. 4A is an example of an electro-anatomical model of a left atrium showing conduction patterns.

FIG. 4B is an example of an electro-anatomical model of the left atrium of FIG. 4A showing a voltage map.

DETAILED DESCRIPTION

Figure 1:
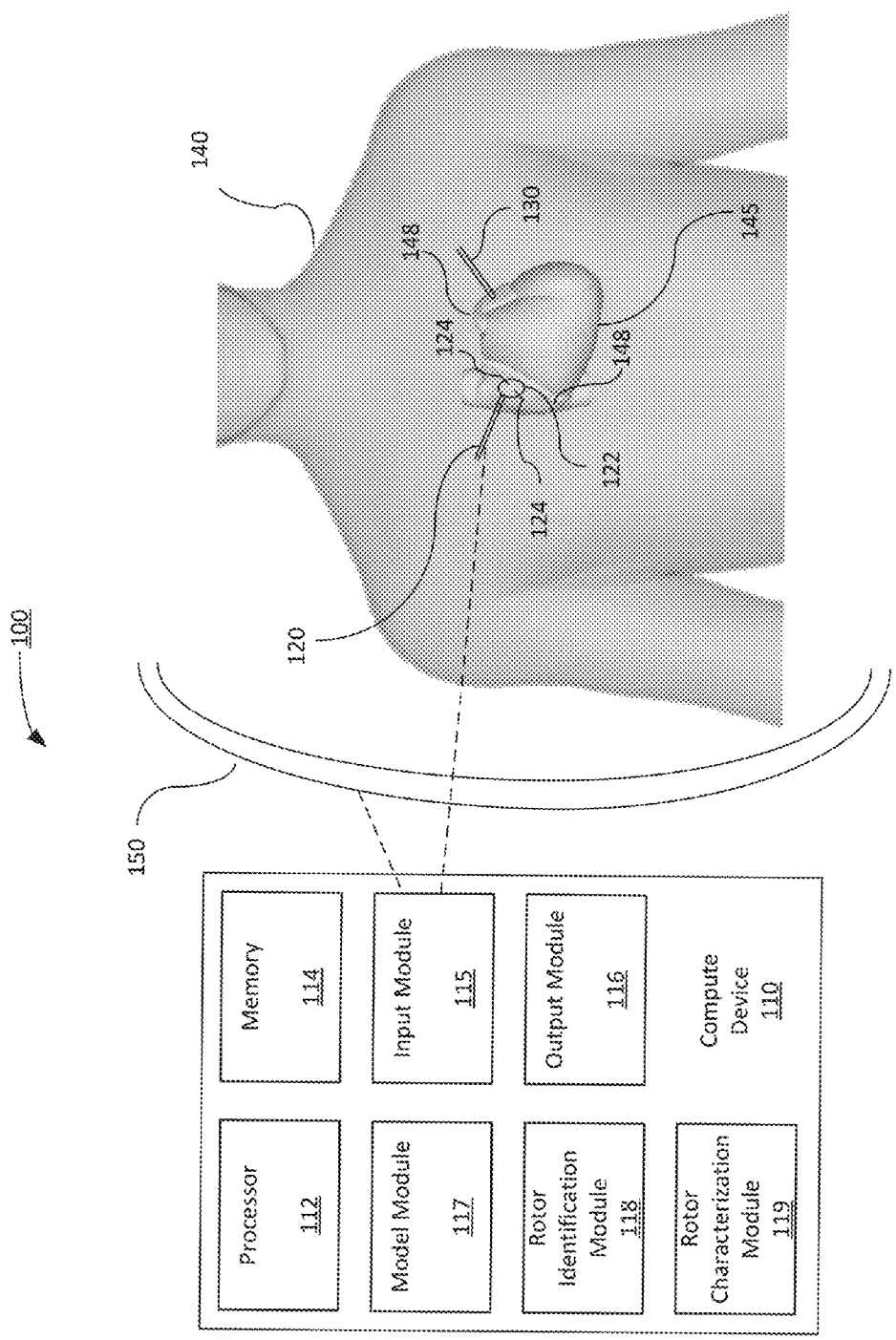
FIG. 1 is a schematic block diagram of a system for classifying and/or treating rotors.

Some embodiments described herein relate to an apparatus including an input module, a model module, and a rotor characterization module. The input module can be operable to receive data from a sensor and/or electrode disposed within a heart of a patient. The model module can define an electro-anatomical model of the heart or a portion thereof based on signals received from the sensor and/or electrode. The electro-anatomical model can include a map of tissue voltages and a map of complex electrogram fractionation. The rotor characterization module can be operable to characterize a rotor as a substrate rotor or a non-substrate rotor based on the electro-anatomical model. The characterization can be based on some combination of rotor stability, the map of tissue voltages, and the map of complex electrogram fractionation.

Some embodiments described herein relate to a method that includes defining an electro-anatomical model of a heart. The electro-anatomical model can include conduction patterns for multiple patterns or phases identified by a measurement instrument. The electro-anatomical model can also include a voltage map of the heart. A portion of the heart containing a rotor can be identified based on circulation in one phase of the model. The rotor can be determined to be stable based on certain characteristics, including the rotor being stable over time. For example, the rotor can be considered stable if circulation appears in multiple phases of the electro-anatomical model. The rotor can be characterized as a substrate rotor based on the rotor being the voltage or a change in voltage at the portion of the heart containing the rotor. For example, the rotor presenting along borders of voltage transition, which can be associated with healthy cardiac tissue meeting scar tissue, can be considered when evaluating a rotor. Furthermore, in some instances, complex fractionated electrograms in the region of the rotors presentation can be evaluated. Complex fractionated electrograms can be negatively associated with substrate rotors. The rotor can be treated or ablated when the rotor is determined to be a substrate rotor.

Some embodiments described herein relate to a method that includes defining an electro-anatomical model of a heart. The electro-anatomical model can include conduction patterns for multiple patterns or phases identified by a measurement instrument. The electro-anatomical model can also include a complex fractionated electrogram map of the heart. A portion of the heart containing a rotor can be identified based on circulation in one phase of the model. The rotor can be determined to be unstable based on that portion of the heart not having circulation in another phase of the conduction model. The rotor can be characterized as a substrate rotor based on the rotor being stable and based on the degree of complex fractionation of the electrogram at the portion of the heart containing the rotor. The rotor can be treated or ablated based on the rotor being a substrate rotor.

FIG. 1 is a schematic block diagram of a system 100 for measuring, detecting, classifying, and/or treating cardiac arrhythmias, according to an embodiment. The system 100 includes a compute device 110 and an imaging device 150. The compute device 110 can operably coupled to a patient 150, e.g., via a sensor 120, and/or the imaging device 150.

The system 100 can also include an instrument 130 configured to be disposed within the heart 145. The instrument 130 can be operable to modify, ablate, and/or burn tissue (e.g., cardiac tissue), for example, to treat atrial fibrillation. In some instances, the instrument 130 can be directed, in whole or in part, by the compute device 110. For example, the compute device 110 can be operable to actuate a portion (e.g., a tip) of the instrument 130 to modify tissue, steer the instrument 130, and so forth. In some instances, the compute device 110 can be operable to provide directions, instructions, and/or data to an operator of the instrument 130 to aid the operator (e.g., a surgeon) in controlling the instrument 130.

The imaging device 150 can be any suitable medical or other imaging device, such as an x-ray device, an ultrasound, magnetic resonance imaging (MRI) device, and/or computerized tomography (CT) imaging device. The imaging device can be operable to image the patient 140, or a portion thereof, such as a heart 145 of the patient 140. In some embodiments, the imaging device 150 can be operable to conduct measurements and process imaging data. For example, the imaging device 150 can include a processor and/or a memory (not shown) which can be structurally and/or functionally similar to a processor 112 and/or a memory 114 of the compute device 110, described in further detail herein.

In some embodiments, the imaging device 150 can be configured to image the heart 145, a chamber of the heart 145, such as an atrium 148, and/or the sensor 120, for example, within the heart 145. In such an embodiment, the imaging device 150 can be operable to localize the sensor 120 within the heart 145. For example, the imaging device 150 can be operable to identify the position of the sensor 120 while the sensor 120 is used to sense electrical or other signals from cardiac tissue. In this way, data received from the sensor 120 can be mapped to specific points and/or areas of the heart 145.

The sensor 120 can be can be a loop catheter with one or more electrodes 124, a basket catheter with one or more electrodes 124, or another type of single- or multi-electrode device capable of sensing cardiac electrical activity locally at particular sites within the heart 145. In some embodiments, the sensor 120 can be a basket catheter designed to fill a heart chamber (e.g., an atrium 148). In other embodiments the sensor 120 can be a basket catheter designed to partially fill a heart chamber. In yet other embodiments, the sensor 120 can be a star shaped catheter.

In some embodiments, the sensor 120 can be or include a near-field measurement instrument having an integrated electromagnetic sensor (not shown) such that the near-field measurement instrument can be localized by a tracking system. The near-field measurement instrument can rove a portion of the patient's 140 anatomy, such as an atrium 148 (e.g., in atrial fibrillation). The near-field measurement instrument can be localized by any suitable tracking system such as tracking systems that utilize electropotential, impedance, or other technologies. For example, the tracking system any of the systems disclosed in United States Patent Application Publication No. 2013/0267835 to Edwards, entitled "System and Method for Localizing Medical Instruments during Cardiovascular Medical Procedures," the disclosure of which is hereby incorporated by reference in its entirety.

In some embodiments, the sensor 120 can be or include a far-field measurement instrument such as a coronary sinus catheter or multiple electrodes placed on the body surface of the patient 140 with the capability of sensing cardiac electrical activity from a distance. Such a far-field measurement instrument can be used to measure the patient's 140 heart signal. The far-field measurement instrument can have an electromagnetic sensor integrated into it such that the far-field measurement instrument can be localized by a tracking system. The far-field measurement instrument can also be localized by other tracking systems that utilize electropotential, impedance, or other technologies for tracking.

The compute device 110 can be any suitable computing entity, such as a desktop computer, laptop computer, server, computing cluster, special purpose instrument, etc. The compute device 110 includes a processor 112, a memory 114, an input module 115, an output module 116, a model module 117, a rotor identification module 118, and a rotor characterization module 119, each of which can be operably and/or communicatively coupled to each other.

The processor 112 can be for example, a general purpose processor, a Field Programmable Gate Array (FPGA), an Application Specific Integrated Circuit (ASIC), a Digital Signal Processor (DSP), and/or the like. The processor 112 can be configured to retrieve data from and/or write data to memory, e.g., the memory 114, which can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth.

The input module 115 can be hardware and/or software (e.g., stored in the memory 114 and/or executing on the processor 112) operable to receive signals from any suitable input device. For example, the input module 115 can be operable to receive data from the sensor 120 associated with electrical features of the heart 145. The input module 115 can further be operable to receive raw and/or pre-processed data from the imaging device 150. For example, as described in further detail herein, the input module 115 can be operable to receive data from the imaging device 150 such that the compute device 110 can construct a model of the heart 145. The input module 115 can further be operable to receive data from an instrument localization device (e.g., the imaging device 150 or any other suitable tracking system). For example, as described in further detail herein, the input module 115 can be operable to receive data from an instrument localization device such that the compute device 110 can associate data received from the instrument 120 with a location at which a measurement was taken. In addition or alternatively, the input module 115 can be operable to receive data from any other suitable input device such as a keyboard, a mouse, a touch screen, etc.

The output module 116 can be hardware and/or software (e.g., stored in the memory 114 and/or executing on the processor 112) operable to send signals from any suitable output device. For example, the output module 116 can be operable to send signals to a monitor (not shown) or other display device to cause the monitor to present an electro-anatomical model of the heart 145. As described in further detail herein, such an electro-anatomical model can indicate the position of rotors and/or can distinguish between substrate and non-substrate rotors. Such a monitor presenting such a graphical electro-anatomical model can be used by a clinician (e.g., a surgeon) to guide and/or direct a cardiac intervention or other procedure.

As another example, the output module 116 can be operably coupled to the instrument 130 and can be operable to actuate the instrument 130 when the instrument 130 is in a position determined by the compute device 110 to be associated with a substrate rotor (e.g., to ablate the rotor). Conversely, the output module 116 can be operable to refrain from actuating the instrument 130 when the instrument 130 is in a position not associated with a rotor and/or determined by the compute device 110 to be associated with a non-substrate rotor. Furthermore, in some embodiments, the output module 116 can be operable to control, steer, and/or direct the instrument 130 to a position determined by the compute device 110 to be associated with a substrate rotor. In addition or alternatively, the output module 116 can be operable to send data to any other suitable output device, such as an audible output device, a chart recorder, a haptic feedback device (e.g., coupled to the instrument 130), etc.

The model module 117, as described in further detail herein, can be operable to generate an electro-anatomical model of a portion of the patient's 140 anatomy, such as the heart 145 and/or an atrium 148. The model module 117 can be hardware and/or software (e.g., stored in the memory 114 and/or executing on the processor 112) operable to receive and/or process data from the sensor 120, the imaging device 150, and/or an instrument tracking device (not shown) (e.g., via the input module 115). The model module 117 can integrate electrical data received from the sensor 120, positional data received from the tracking device, and/or anatomical data received from the imaging device 150 to generate a unified and/or layered electro-anatomical model. In addition or alternatively, the model module 117 can be operable to define multiple electro-anatomical models, for example, associated with different electric or anatomical features, such as voltage, conduction patterns, and/or complex electrogram fractionation.

The rotor identification module 118 can be hardware and/or software (e.g., stored in the memory 114 and/or executing on the processor 112) operable to process electrical and/or anatomical data pre-processed, for example, by the model module 117. The rotor identification module 118, as described in further detail herein can be operable to identify the presence and/or position of rotors. For example, the rotor identification module 118 can be operable to identify swirling and/or spiral conduction patterns associated with rotors.

The rotor characterization module 119 can be hardware and/or software (e.g., stored in the memory 114 and/or executing on the processor 112) operable to process electrical and/or anatomical data pre-processed, for example, by the rotor identification module 118 and/or the model module 117. The rotor characterization module 119, as described in further detail herein, particularly with reference to FIG. 5, can be operable to process rotor stability data, voltage data, complex fractionated electrograms (CFEs), and/or any other suitable date to characterize a rotor as a substrate rotor or a non-substrate rotor.

Figure 2:
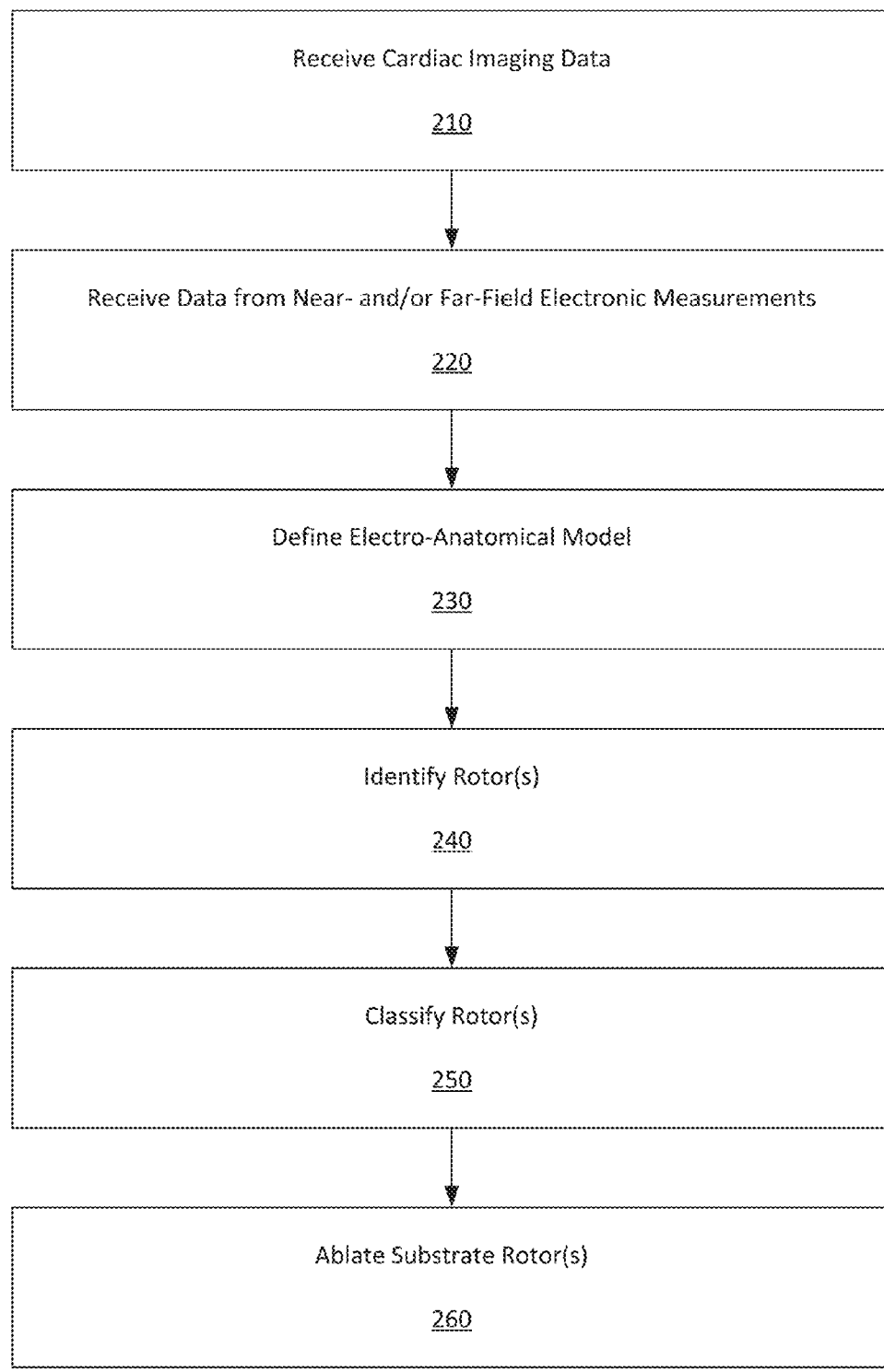
FIG. 2 is a flow chart of a method of treating a cardiac arrhythmia, according to an embodiment.

FIG. 2 is a flow chart of a method of treating cardiac arrhythmia, according to an embodiment. In some instances, the method of FIG. 2 can be a computer-implemented method, that is a method stored in a non-transitory memory and/or executing on a processor. For example, the method of FIG. 2 can be executed by the compute device 110, shown and described above with reference to FIG. 1.

At 210, cardiac imaging data can be received. The cardiac imaging data can be data created from a cluster of two-dimensional (2D) or three-dimensional (3D) points created by tracking an instrument (e.g., the sensor 120) inside the heart as it is used to paint the interior surface of a chamber, and/or data from an imaging device (e.g., the imaging device 150). In some embodiments, the imaging data can be suitable to generate, define, and/or render a 3D model of the heart, for example, using various linear and non-linear 3D registration techniques. In some embodiments, the imaging data can include time data such that a four-dimensional (4D) model of the heart can be generated, defined, and/or rendered. For example, a video, real-time, and/or animated model of the heart can be created using the cardiac imaging data received, at 210.

At 220, near- and/or far-field cardiac date (e.g., cardiac electrogram (EGM) data) can be received. For example, a near-field measurement instrument (e.g., the sensor 120) can be used to measure a patient's heart signal. The near-field measurement instrument can include and/or have an electromagnetic sensor integrated into it such that the near-field measurement instrument can be localized by a tracking system. In addition or alternatively, a far-field measurement instrument such as a coronary sinus catheter or multiple electrodes placed on the body surface of the patient with the capability of sensing cardiac electrical activity from a distance can also be used to measure the patient's heart signal. The far-field measurement instrument can include and/or have an electromagnetic sensor integrated into it such that the far-field measurement instrument can be localized by a tracking system. The far-field measurement instrument can also be localized by other tracking systems that utilize electropotential, impedance, or other technologies for tracking.

The near-field measurement instrument can capture EGM or other cardiac data at various locations and/or positional data in x-y-z space, which can be received at 220 and integrated with the imaging data received at 210. The near-field measurement data can be stored in a computer memory, database or other suitable device for storing data (e.g., the memory 114). Furthermore, the far-field instrument can capture data associated with each near-field measured point, which can also be received at 220 can also be integrated with the imaging data received at 210. The far-field data can also be stored in a computer memory, database, or other suitable device for storing data (e.g., the memory 114).

At 230, the electrogram data received, at 220 and the imaging data received, at 210 can be combined or integrated to define an electro-anatomical model. For example, the model module 117 can be operable to define an electro-anatomical model based on imaging data received at 210 and near-filed and/or positional data received at 220. The electro-anatomical model can be a 3D or 4D model of a heart or a portion thereof including a visualization (e.g., a vector field, heat map, and/or any other suitable visualization) of electric potentials, conduction patterns or velocities, and/or any other suitable electroanatomic feature, such as, for example, complex fractionated electrogram mapping.

FIGS. 3A-4B are examples of 3D left atrial electro-anatomical models. FIGS. 3A and 3B are two example phases of the electro-anatomical models of a left atrium showing cardiac conduction patterns. The conduction patterns can cause contraction of heart muscle. As described in further detail herein, a substrate based rotor 310, characterized by a swirling conduction pattern, is indicated in the phase depicted in FIG. 3A as well as in the phase depicted in FIG. 3B. A non-substrate based rotor 320 is shown in FIG. 3A. The phase depicted in FIG. 3B does not indicate a swirling conduction pattern associated with rotor 320.

FIG. 3C is the left atrium of FIGS. 3A and 3B showing a voltage map of the left atrium. The voltage map of FIG. 3C highlights areas of healthy tissue versus scar or unhealthy tissue. FIG. 3D is the left atrium of FIGS. 3A-3C with a complex fractionated atrial electrogram map (CFAE). The CFAE map shown in FIG. 3D highlights areas having noisy (or high) fractionation of electrograms (EGMs) versus areas with less fractionation of EGMs.

FIG. 4A is an electro-anatomical model of a left atrium showing cardiac conduction patterns. FIG. 4A depicts two non-substrate based rotors 420 and one substrate based rotor 410 characterized by swirling conduction vectors. FIG. 4B is the left atrium of FIG. 4A showing a voltage map highlighting borders of healthy tissue meeting scar or dead tissue resulting in voltage transition deltas. As described in further detail herein, the presence of rotor 410 in a voltage transition region 470 is indicative of rotor 410 being a substrate based rotor. Treatment (ablation) of the non-substrate based rotors 420 indicated by dots 465 did not improve cardiac rhythm. Ablation of the substrate-based rotor 410 indicated by dots 460 resulted in significant improvements in heart rhythm change and termination of atrial fibrillation.

Returning to FIG. 2, a control unit (e.g., the model module 117) can identify patterns on the far-field data and index near-field cardiac electrical data and near-field instrument position location information to far-field data patterns at 230. The control unit can organize a set of near-field cardiac electrical data from multiple near-field position locations that display the same far-field data patterns. The control unit can use this set of data and various interpolation techniques to generate a 3D map of electrical activity for a region of the heart corresponding to that far-field data pattern. This process can be repeated for multiple far-field data patterns to create multiple maps. The multiple 3D maps can be sequenced by the control unit into a 4D map to show the various states of electrical conductivity of the heart over time.

The 3D and/or 4D maps created can be superimposed on the model of the patient's heart. The 3D maps can be displayed in 3D for visualization with bi-color glasses, polarized glasses, shuttered glasses, or any other suitable viewing device that can be used to give true 3D perspective to the viewer.

At 240, rotors can be identified (e.g., by the rotor identification module 118). Rotors can be identified by any suitable technique. For example, rotors can be identified using a computational mapping algorithm to, for example, integrate spatiotemporal wave front patterns during atrial fibrillation on the electro-anatomical map defined, at 230. For example, the computational mapping algorithm can search the surface of the model defined 230 for complete rotation of conduction velocity vectors. In some embodiments the complete surface of the model can be searched and one or more rotors can be identified. In some embodiments, when a rotor is identified, the region of rotation associated with the rotor can be searched for additional rotations (e.g., partial and/or complete rotations), for example, over all phases. In addition or alternatively, voltage transition zones can be located and identified, for example, within a region of rotation. In some instances, several rotors can be identified associated with a voltage transition zone within a region of rotation. In some embodiments, information such as: (1) the number (or percent) of phases in which the rotor is identified, (2) change in voltage at the region containing the rotor and/or between the rotor and an adjacent region, and/or (3) degree of complex fractionation for the region containing the rotor can be calculated and/or determined for each rotor.

At 250, rotors can be classified as substrate rotors or non-substrate rotors (e.g., by the rotor characterization module 119). For example, rotors can be classified as shown and described in further detail herein with reference to FIG. 5. Rotors that are classified as substrate rotors can be associated with causing and/or driving arrhythmias, while rotors that are classified as non-substrate rotors may not be associated with an arrhythmia.

Rotors classified as substrate rotors, at 250, can be selected for treatment and/or treated, at 260. For example, substrate rotors can be ablated. Treatment of substrate rotors, at 260, is strongly correlated with improved cardiac rhythms. Non-substrate rotors may not be treated, at 260. Treatment of non-substrate rotors is not correlated with, or is only weakly correlated with improved cardiac rhythms. In an embodiment where only substrate rotors are treated, treatment time can be reduced and/or more cardiac tissue can be preserved as compared to an embodiment where substrate and non-substrate rotors are treated.

Figure 5:
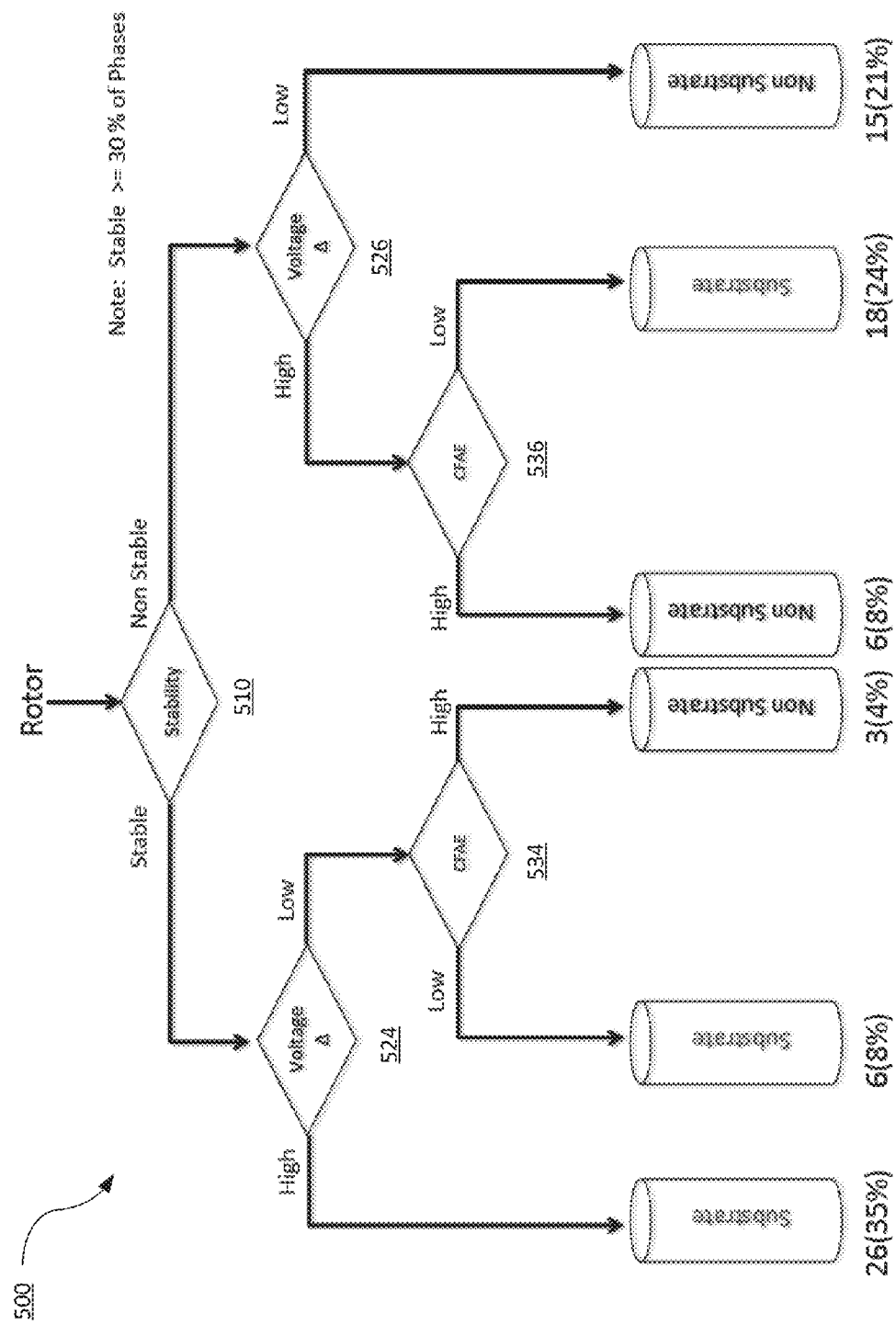
FIG. 5 is a flow chart of a method for classifying rotors, according to an embodiment.

FIG. 5 is a decision tree 500 for classifying rotors, according to an embodiment. For example, the decision tree 500 can be used to classify rotors as substrate or non-substrate rotors, at 250, as shown and described above with reference to FIG. 2. In some instances, rotors can be classified based on three criteria, stability, voltage change, and complex fractionation level. In some instances, rotors can also be classified based on rotational patterns of wavefronts or any other suitable feature. It should be appreciated that additional criteria can be considered and/or different means can be employed to classify rotors.

At 510, a rotor can be evaluated for stability based, for example, on determining how many phases out of a total number of phases in which the rotor appears. A phase can be a distinct pattern identified by a far-field electrogram measurement instrument. A rotor that presents in 10% or more, 20% or more, 30% or more, 50% or more, or any other suitable proportion of the total phases can be considered to be stable.

After evaluating for stability, at 510, rotors can be evaluated based on whether they are in a voltage transition zone. A voltage transition zone is a region of the heart characterized by a relatively large change in electrical potential (high ΔV) over a relatively short distance. In some cases, a voltage transition zone can be a region of the heart where scar tissue, which may be characterized by relatively low voltages, is directly adjacent to healthy tissue, which may be characterized by relatively higher voltages. As measured in atrial fibrillation, a change of greater than 0.5 mV, a change of greater than 0.23 mV, a change of greater than 0.2 mV, a change of greater than 0.1 mV, or any other suitable threshold can be determined to be a high voltage transition. A voltage transition zone can be associated with healthy tissue meeting dead or scarred tissue. As an illustration, rotor 310 is migrating along a voltage transition zone, as shown in FIG. 4A, while rotor 320 is not disposed in a voltage transition zone.

Rotors determined to be stable, at 510, are evaluated for voltage transition, at 524. If a rotor is stable and in a voltage transition zone, such as rotor 410, it can be classified as a substrate rotor. Rotors that are determined to be unstable, at 510, are evaluated for voltage transition, at 526. If a rotor is unstable and not in a voltage transition zone, such as rotor 320, the rotor can be classified as a non-substrate rotor.

If a rotor is stable and not in a voltage transition zone or unstable and in a voltage transition zone, at 534 or 536, respectively, complex fractionation (CFAE) level can be evaluated in the region in which the rotor presents. Evaluating CFAE can include identifying, all peaks of bipolar electrogram deflections which fall into the voltage window of 0.05 to 0.15 mV, −0.05 to −0.15 mV, and those exceed +/−0.15 mV. The intervals between two successive deflection peaks falling into the voltage window of 0.05 to 0.15 mV or −0.05 to −0.15 mV can be determined. The CFAE level can be defined as the number of such intervals between 70 ms and 120 ms in length during a 2.5 second measurement. A CFAE level of 4, 5, 6, or any other suitable level can be considered to be high complex fractionation.

A stable rotor that does not present in a voltage transition zone, or an unstable rotor that presents in a voltage transition zone, with a low complex fractionation can be classified as a substrate rotor at 534 or 536. Conversely, such a rotor with high complex fractionation can be classified as a non-substrate rotor at 534 or 536.

While various embodiments have been described above, it should be understood that they have been presented by way of example only, and not limitation. Furthermore, although various embodiments have been described as having particular features and/or combinations of components, other embodiments are possible having a combination of any features and/or components from any of embodiments where appropriate as well as additional features and/or components.

Where methods described above indicate certain events occurring in certain order, the ordering of certain events may be modified. Additionally, certain of the events may be performed repeatedly, concurrently in a parallel process when possible, as well as performed sequentially as described above. Where methods are described above, it should be understood that the methods can be computer implemented methods having instructions stored on a non-transitory medium (e.g., a memory) and configured to be executed by a processor. For example, some or all of the events shown and described with reference to FIGS. 2 and/or 5 can be implemented on a computer (e.g., the compute device 110).

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. An apparatus, comprising:
   an input module, the input module configured to receive data from an electrode disposed within a heart;
   a model module operably coupled to the input module, the model module configured to define an electro-anatomical model of at least a portion of the heart, the electro-anatomical model including a map of tissue voltages and a map of complex electrogram fractionation based on signals received from the electrode; and
   a rotor characterization module operably coupled to the model module, the rotor characterization module configured to characterize a rotor as a substrate rotor or a non-substrate rotor based on at least two of (1) rotor stability, (2) the map of tissue voltages at the rotor, and (3) the map of complex electrogram fractionation at the rotor.

2. The apparatus of claim 1, further comprising a rotor identification module operably coupled to the model module, the rotor identification module configured to identify rotors based on conduction patterns from the electro-anatomical model.

3. The apparatus of claim 1, further comprising a rotor identification module operably coupled to the model module, the rotor identification configured to identify rotors based on identifying circulating conduction patterns from the electro-anatomical model.

4. The apparatus of claim 1, further comprising a rotor identification module operably coupled to the model module, the rotor identification module configured to identify a portion of the heart containing the rotor in a first phase of the electro-anatomical model, the rotor identification module configured to identify the rotor as unstable based on the rotor identification module not identifying the rotor in the portion of the heart in a second phase of the electro-anatomical model,
   the rotor characterization module configured to characterize the rotor as a substrate rotor or a non-substrate rotor based, in part, on the rotor being unstable.

5. The apparatus of claim 1, fin her comprising a rotor identification module operably coupled to the model module, the rotor identification module configured to identify a portion of the heart containing the rotor in a first phase of the electro-anatomical model, the rotor identification module configured to identify the rotor as stable based on the identification module identifying the rotor in the portion of the heart in a second phase of the electro-anatomical model,
   the rotor characterization module configured to characterize the rotor as a substrate rotor or a non-substrate rotor based, in part, on the rotor being stable.

6. The apparatus of claim 1, wherein the rotor characterization module is configured to identify the rotor as a substrate rotor based, at least in part, on (1) the rotor being stable and (2) the rotor being in a high voltage transition zone on the map of tissue voltages.

7. The apparatus of claim 1, wherein the rotor characterization module is configured to identify the rotor as a substrate rotor based, at least in part, on (1) the rotor being stable, (2) the rotor being in a low voltage transition zone on the map of tissue voltages, and (3) the rotor being in a zone of low complex fractionation on the map of complex electrogram fractionation.

8. The apparatus of claim 1, wherein the rotor characterization module is configured to identify the rotor as a non-substrate rotor based, at least in part, on (1) the rotor being stable, (2) the rotor being in a low voltage transition zone on the map of tissue voltages, and (3) the rotor being in a zone of high complex fractionation on the map of complex electrogram fractionation.

9. The apparatus of claim 1, wherein the rotor characterization module is configured to identify the rotor as a non-substrate rotor based, at least in part, on (1) the rotor being unstable, (2) the rotor being in a high voltage transition zone on the map of tissue voltages, and (3) the rotor being in a zone of high complex fractionation on the map of complex electrogram fractionation.

10. The apparatus of claim 1, wherein the rotor characterization module is configured to identify the rotor as a substrate rotor based, at least in part, on (1) the rotor being unstable, (2) the rotor being in a high voltage transition zone on the map of tissue voltages, and (3) the rotor being in a zone of low complex fractionation on the map of complex electrogram fractionation.

11. The apparatus of claim 1, wherein the rotor characterization module is configured to identify the rotor as a non-substrate rotor based, at least in part, on (1) the rotor being unstable, and (2) the rotor bring in a low voltage transition zone on the map of tissue voltages.

12. The apparatus of claim 1, further comprising an output module configured to send a signal such that an optical display presents a visualization of the heart including a substrate rotor.

13. The apparatus of claim 1, further comprising a surgical instrument configured to ablate a substrate rotor.

14. The apparatus of claim 13, wherein the surgical instrument is configured to not ablate a non-substrate rotor.

15. The apparatus of claim 1, wherein the input module is configured to receive data from a plurality of electrodes of a roving medical instrument disposed within a heart chamber.

16. The apparatus of claim 1, wherein the input module is configured to receive data from the electrode disposed within an atrium of the heart when the heart is in atrial fibrillation.

17. A non-transitory processor readable medium storing code representing instructions to be executed by a processor, the code comprising code to cause the processor to:
define an electro-anatomical model of a heart including conduction patterns for a plurality of phases of the heart and a voltage map;
identify a portion of the heart containing a rotor based on circulation in a conduction pattern for a first phase from the plurality of phases;
identify the rotor as stable based on circulation in a conduction pattern for be portion of the heart in a second phase from the plurality of phases;
characterize the rotor as a substrate rotor based, at least in part, on (1) the rotor being stable and (2) a change in voltage at the portion of the heart; and
send a signal to cause the rotor to be treated based on the rotor being a substrate rotor.

18. The non-transitory processor readable medium of claim 17, wherein the code to cause the processor to identify the rotor as stable includes code to cause the processor to identify the rotor as stable based on circulation in conduction patterns for the portion of the heart in a subset of the plurality of phases, the subset of the plurality of phases including the first phase and the second phase, the subset of the plurality of phases making up at least 30% of the plurality of phases.

19. The non-transitory processor readable medium of claim 17, wherein there is a voltage change of at least 0.23 mV at the portion of the heart.

20. The non-transitory processor readable medium of claim 17, wherein:
the electro-anatomical model of the heart further includes a complex fractionated atrial electrogram map; and
the rotor is characterized as a substrate rotor based on a voltage change of less than 0.23 my at the portion of the heart and the portion of the heart having low complex fractionation on the complex fractionated atrial electrogram map.

21. A method, comprising:
defining an electro-anatomical model of a heart including conduction patterns for a plurality of phases of the heart and a complex fractionated atrial electrogram map;
identifying a portion of the heart containing a rotor based on circulation in a conduction pattern for a first phase from the plurality of phases;
identifying the rotor as unstable based on a lack of circulation in a conduction pattern for the portion of the heart in a second phase from the plurality of phases;
characterizing the rotor as a substrate rotor based, at least in part, on (1) the rotor being unstable and (2) the portion of the heart having low complex fractionation on the complex fractionated atrial electrogram map; and
treating the rotor based on the rotor being a substrate rotor.

22. The method of claim 21, wherein:
the electro-anatomical model of the heart further includes a voltage map; and
the rotor is characterized as a substrate rotor based, in part, on a high change in voltage at the portion of the heart.

23. The method of claim 21, wherein treating the rotor includes ablating the rotor.

24. The method of claim 21, wherein the portion of the heart contains a first rotor, and the electro-anatomical model of the heart further includes a voltage map the method further comprising:
identifying a second portion of the heart containing a second rotor;
characterizing the second rotor as a non-substrate rotor based on at least two of (1) the stability of the second rotor, (2) the voltage map at the second portion of the heart, and (3) the map of complex electrogram fractionation at the second portion of the heart; and
not treating the second rotor based on the second rotor being characterized as a non-substrate rotor.

* * * * *